US007601684B2

(12) United States Patent
Roddiger et al.

(10) Patent No.: US 7,601,684 B2
(45) Date of Patent: *Oct. 13, 2009

(54) DIAGNOSIS AND TREATMENT OF DISORDERS OF IRON METABOLISM

(75) Inventors: Ralf Roddiger, Gorxheimertal (DE); Paul Lehmann, Worms (DE); Lothar Thomas, Frankfurt (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/242,061

(22) Filed: Sep. 12, 2002

(65) Prior Publication Data

US 2003/0073635 A1  Apr. 17, 2003

Related U.S. Application Data

(60) Provisional application No. 60/322,526, filed on Sep. 14, 2001.

(51) Int. Cl.
*G01N 33/48* (2006.01)
*G01N 33/49* (2006.01)
*G01N 33/543* (2006.01)
*A61K 38/00* (2006.01)
*C07K 14/505* (2006.01)
*G01N 33/566* (2006.01)

(52) U.S. Cl. ............................ 514/2; 435/7.1; 435/7.92; 435/4; 436/8; 436/518; 436/501; 530/397

(58) Field of Classification Search ........................ None
See application file for complete search history.

(56) References Cited

OTHER PUBLICATIONS

Little et al. Hemochromatosis:Diagnosis and Management. American Family Physician, vol. 53/8, pp. 2623-2628 (1996).*
Feelders et al. Regulation of iron metabolism in the acute-phase response:interferon gamma and tumor necrosis factor alpha induce hypoferraemia, ferritin production and a decrease in circulating transferrin receptors in cancer patients. European Journal of Clinical Investigation vol. 28:520-527 (1998).*
Suominen et al. Single values of serum transferrin receptor and transferrin receptor ferritin index can be used to detect true and functional iron deficiency in rheumatoid arthritis patients with anemia. Arthritis and Rheumatism vol. 43/5:1016-1020 (May 2000).*
Lehmann, P. et al. Clinical Chemistry and Laboratory Medicine, 39(Special Supplement), pp. S338, Abstract PO-T011, May 2001.*
Lehmann, P. et al. Onkologie, 23(Sonderheft 7), p. 193, A bstract 0742, Oct. 2000.*
Thomas et al., Clinical Chemistry, 48(7):1066-1076, 2002.*
Lehmann et al., Clinical Chemistry, 48(6, supplement), pp. A33-A34, Abstract A-103, 2002.*

Looker et al. Increased serum transferrin saturation is associated with lower serum transferrin receptor concentration. Clinical Chemistry, 45:12, pp. 2191-2199 (1999).*
Fishbane et al. Reticulocyte hemoglobin content in the evaluation of iron status of hemodialysis patients. Kidney International, vol. 52, pp. 217-222 (1997).*
Remacha et al. The role of serum transferrin receptor in the diagnosis of iron deficiency. Haematologica 83:963-966 (1998).*
Bovy, et al., *Factors determining the percentage of hypochromic red blood cells in hemodialysis patients*, Kidney International, vol. 56, pp. 1113-1119 (1999).
Tessitore, et al., *The role of iron status markers in predicting response to intravenous iron in haemodialysis patients on maintenance erythropoietin*, Nephrology Dialysis Transplantation, vol. 16, pp. 1416-1423 (2001).
Thomas, et al., *Biochemical Markers and Hematologic Indices in the Diagnosis of Functional Iron Deficiency*, Clinical Chemistry, vol. 48, pp. 1066-1076 (2002).
Hasegawa, Midori, et al., Evaluation of reticulocyte hemoglobin content, percentage of hypochromic red blood cells, and ratio of serum transferring receptor level/serum iron level as markers of iron-deficiency erythropoiesis in patients undergoing hemodialysis, NLM Database accession No. NLM12216478 XP002247472 abstract of Nippon Jinzo Gakkai Shi, Japan 2002, vol. 44. No. 5, pp. 453-463, ISSN: 0385-2385.
Suominen, Pauli, et al., *Single Values of Serum Transferrin Receptor and Transferrin Receptor Ferritin Index Can be Used to Detect True and Functional Iron Deficiency in Rheumatoid Arthritis Patients with Anemmia*, Arthritis & Rheumatism, 43:1016-1020 (2000).
Feelders, R.A., et al., *Regulation of iron metabolism in the acute-phase response: interferon γ and tumour necrosis factor α induce hypoferraemia, ferritin production and a decrease in circulating transferrin receptors in cancer patients*, European Journal of Clinical Investigation, 28:520-527 (1998).
Looker, A., et al., *Increased Serum Transferrin Saturation Is Associated with Lower Serum Transferrin Receptor Concentration*, Clinical Chemistry, 45:2191-2199 (1999).
Beguin, Y., et al., *Acute functional iron deficiency in obese subjects during a very-low energy all-protein diet*, American Journal of Clinical Nutrition, 66:75-79 (1997).
Fishbane, S., et al., *Reticulocyte hemoglobin content in the evaluation of iron status of hemodialysis patients*, Kidney International, 52:217-222 (1997).

\* cited by examiner (Continued)

*Primary Examiner*—Marianne P Allen
*Assistant Examiner*—Regina M DeBerry
(74) *Attorney, Agent, or Firm*—McDonnell, Boehnen, Hulbert & Berghoff, LLP

(57) ABSTRACT

The invention concerns a method for detecting disorders of iron metabolism and in particular the differential diagnosis of disorders of iron metabolism by means of three independent parameters. The differential diagnosis can be used to classify disorders of iron metabolism and to recommend the required treatment and to monitor the progress and response to treatment.

12 Claims, 4 Drawing Sheets

Anaemia program

Sender (external)

Roche Diagnostics GmbH
Sandhofer Strasse 116
D-68305 Mannheim

Hospital Ward

Telephone

Patient

Sample receive

Preanalysis:
Biochemical parameters:
Blood count:

☐ Serum
☐ EDTA plasma

Proteins:
sTfR (anaemia protein)
Ferritin
CRP data input

Reference range:
Women (premenopausal):
Men:
Women (premenopausal)
Men:
(consensus value):

Haematology:
haematoglobin
erythrocytes
haematocrit
MCV
MCH data input

Parenteral iron supply:
Hb measured
Hb target value
Hb deficiency
weight
blood volume
Fe reserves in Hb
Fe reserves in depots data input Erythropoietin dose: data input

[Graph: CRP [mg/L] vs sTfR [mg/L] / Log Ferritin [µg/L], with quadrants A, B, C, D at boundaries 0.9, 3.4–3.7, 10, >100]

| Quadrant | Disorders of iron metabolism | sTfR/log ferritin | CRP concentration | Therapy |
|---|---|---|---|---|
| A: | disorders of iron distribution (potential) | < 3.7 (women) < 3.4 (men) | > 5 mg/l | dependency on the reticulocyte count: erythropoietin dose |
| B: | iron overloading | < 0.9 (women + men) | < 5 mg/l | blood letting |
| C: | normal iron status | 0.9 – 3.7 (women) 0.9 – 3.4 (men) | < 5 mg/l | |
| D: | iron deficiency | > 3.7 (women) > 3.4 (men) | <> 5 mg/l | iron substitution |

Assessment:

Recommended treatment:

FIGURE 2

Differential Diagnosis and Monitoring of disorders of iron metabolism

DIAGNOSIS AND TREATMENT OF DISORDERS OF IRON METABOLISM

CROSS-REFERENCE TO RELATED APPLICATIONS

This application claims the benefit of U.S. Provisional Patent Application Ser. No. 60/322,526 filed Sep. 14, 2001.

FIELD OF THE INVENTION

The invention concerns a method for detecting disorders of iron metabolism and in particular the differential diagnosis of disorders of iron metabolism by means of three independent parameters. The differential diagnosis can be used to classify disorders of iron metabolism and to recommend the required treatment and to monitor the progress and response to treatment.

BACKGROUND OF THE INVENTION

Iron as a component of haemoglobin and the cell haemins is one of the most important biocatalysts in the human organism. Disorders of iron metabolism and in particular iron deficiency and perturbations of iron distribution and utilization in chronic general illnesses are among the most frequently overlooked or misinterpreted diseases. One of the main reasons for this is that the determination of transport iron in the serum or plasma which is used in conventional diagnostics does not allow a representative estimation of the total body iron stores due to short-term variations.

The ability to precisely determine the iron storage protein ferritin in plasma provided a method for determining the total body iron stores and thus allowed a more rapid and reliable diagnosis especially of iron deficiency states. Ferritin is an indicator of the amount of storage iron. The soluble transferrin receptor (sTfR) indicates the iron requirements of the cell and erythropoiesis activity. The sTfR/log ferritin index is a measure of the depletion of the iron stores and of the functional iron compartments. In chronic inflammatory diseases such as in infections and especially tumour diseases, iron is redistributed with a relative overload of the iron stores accompanied by a relative deficiency of iron supply to the erythropoietic cells.

Due to the very limited capacity to absorb iron, the iron requirements can only be met by recycling functional iron. It is stored in the form of ferritin and haemosiderin. Each cell is able to take up a surfeit of iron by synthesizing ferritin and the basic mechanisms for this are identical in all types of cells. The transferrin-iron$^{3+}$ complex is bound to the transferrin receptor of the cell membrane. The uptake of iron can be regulated by the transferrin receptor expression. In addition iron induces the synthesis of apoferritin. Hence in the majority of metabolic situations a representative proportion of the synthesized ferritin is released into the blood plasma.

However, even if the above-mentioned parameters are employed, it is not in practice possible or very difficult to routinely determine and differentiate between various iron states.

Therefore an object of the present invention was to provide a method which enables the reliable detection of disorders of iron metabolism in a simple manner.

SUMMARY OF THE INVENTION

This object is achieved according to the invention by a method for determining the iron status and in particular for detecting disorders of iron metabolism comprising the determination of:

(i) a parameter which allows a determination of the total body iron stores, (ii) a parameter which allows a determination of the erythropoietic maturation process and/or its activity and (iii) a parameter which allows a determination of unspecific disorders of iron metabolism.

Hence the invention concerns the differential diagnosis of disorders of iron metabolism by means of three independent parameters.

The determination of the total body iron stores can for example be carried out by measuring the parameters erythrocyte ferritin, zinc protoporphyrin, haemoglobin, myoglobin, transferrin and transferrin saturation, ferritin, haemosiderin or/and the enzymes catalase, peroxidase or/and cytochrome. A determination of the concentration or activities of these parameters enables a determination of the total body iron stores which is determined as parameter (i) of the method according to the invention. Ferritin or transferrin and particularly preferably ferritin is used as the parameter.

The erythropoietic maturation process and/or the erythropoietic activity can for example be ascertained or determined using erythrocyte indices, reticulocyte indices, FS-e (forward scatter erythrocytes) and/or the soluble transferrin receptor (sTfR). The amount or concentration of soluble transferrin receptor (sTfR) is particularly preferably determined as parameter (ii) in the method according to the invention and used as a parameter for the erythropoietic maturation process or its activity.

Biochemical parameters as well as haematological parameters can be used as a parameter for determining unspecific disorders of iron metabolism. Acute phase proteins and regulators of acute phase protein synthesis are preferably used as biochemical parameters whereas disorders of reticulocyte synthesis are preferably used as haematological parameters. Examples of acute phase proteins whose amount or concentration is determined in order to determine unspecific disorders of iron metabolism comprise C-reactive protein (CRP), serum amyloid A (SAA), $\alpha_1$-anti-chymotrypsin, acidic $\alpha_1$-glycoprotein, $\alpha_1$-antitrypsin, antitrypsin, haptoglobin, fibrinogen, complement component C3, complement component C4 or/and coeruloplasmin. Examples of regulators of acute phase protein synthesis are interleukin 6 (IL-6), leukaemia inhibiting factor (LIF), oncostatin M, interleukin 11 (IL-11), ciliary neurotropic factor (CNTF), interleukin 1α (IL-1α), interleukin 1β (IL-1β), tumour necrosis factor-α (TNFα), tumour necrosis factor-β (TNFβ), insulin, fibroblast growth factor (FGF), hepatocyte growth factor, transgrowth factor β (TGFβ) or/and interferon.

Disorders of reticulocyte synthesis such as $CH_2$, reticulocyte count, Hb content of reticulocytes (CHr), IRF (immature reticulocyte fraction) new RBC and reticulocyte fluorescence parameters and/or FS-r (forward scatter reticulocytes) are haematological parameters that can be used in particular as parameter (iii) of the method according to the invention. CRP, SAA or/and CHr are preferred.

BRIEF DESCRIPTION OF THE FIGURES

FIG. 2 shows an example of an input for an anaemia program, the classification of the four quadrants A, B, C, D in a diagram of CRP against sTfR/log ferritin, the classification of the squares and the treatment recommended in each case.

DETAILED DESCRIPTION

Figure 1:
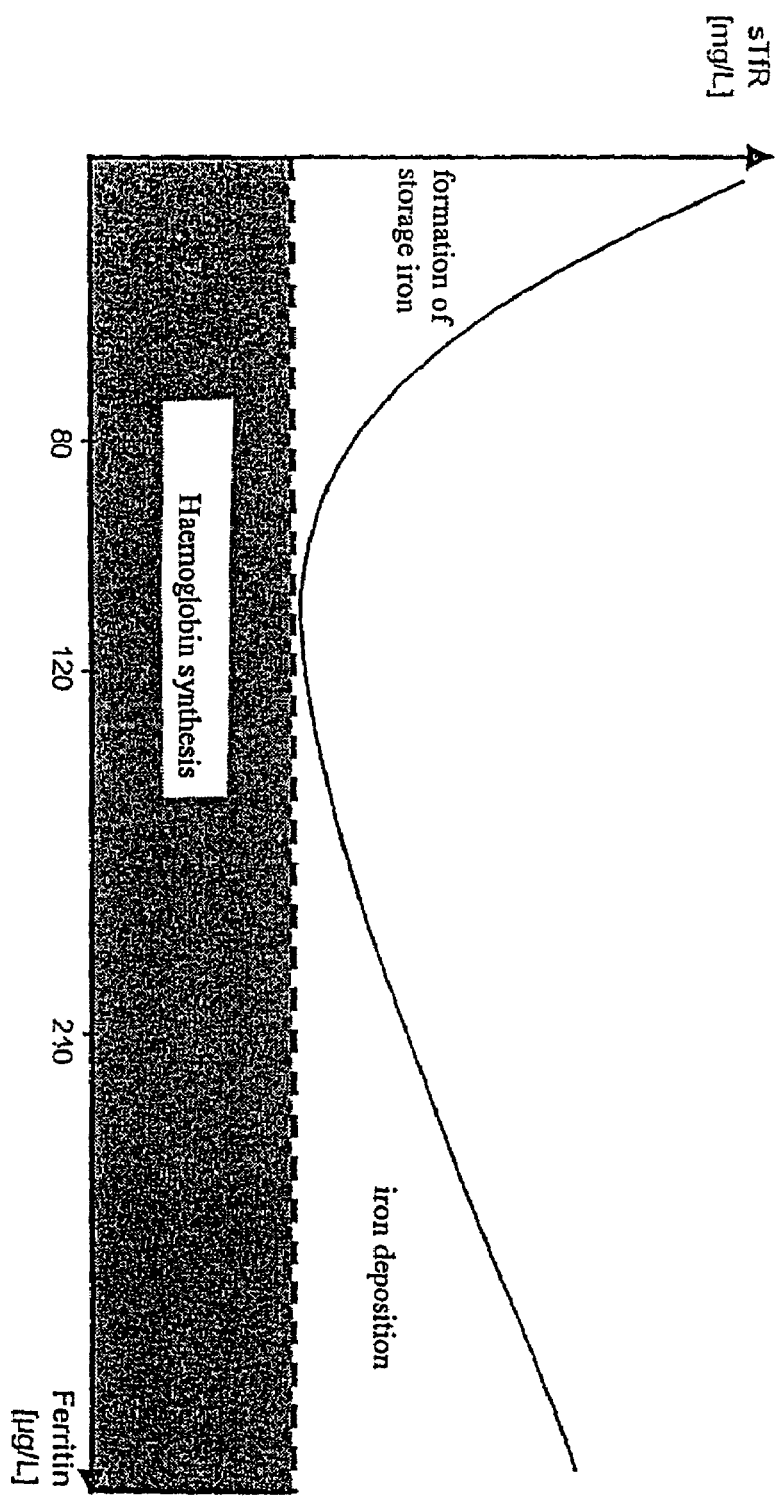
FIG. 1 shows that the soluble transferrin receptor (sTfR) is a parameter for three types of iron status. For (A) (iron distribution disturbance) this means Hb synthesis plus iron deposition, for (B) (iron overloading) Hb synthesis plus iron deposition, for (C) (normal iron status) Hb synthesis and for (D) (iron deficiency) Hb synthesis plus storage iron.

According to the invention it was surprisingly found that rapid and reliable information on the iron status of patients can be obtained by combining three independent parameters. In particular it was found that biochemical or haematological markers and in particular inflammatory markers which are unspecific as such, can be used in an appropriate combination with other parameters to determine the iron status.

In particular the method according to the invention allows a classification of the iron status and in particular of disorders of iron metabolism.

The combination of three independent parameters enables a routine differentiation between normal iron status, iron deficiency, iron distribution disorders and/or iron overloading. In particular the method according to the invention allows a differentiation between normal iron status and iron overloading. In addition it allows a differentiation between the status of iron deficiency and iron distribution disorders. Perturbations of iron distribution can lead to chronic diseases such as rheumatism, asthma or tumours and hence an early detection of iron distribution disorders is of particular importance.

In a particularly preferred embodiment the iron status determined by the method according to the invention is classified in one of the following groups:
(A) iron distribution disorder or/and iron utilization disorder with acute phase reaction,
(B) iron overloading,
(C) normal iron status, and
(D) deficiency of storage iron.

The evaluation of the determined parameters can be preferably assisted by a computer for example by use of an anaemia program. Furthermore the determined measurements are preferably represented graphically in the form of diagrams in order to easily assign the measuring ranges to the various iron states. For example parameter (iii) can be plotted on the ordinate and the ratio of parameter (ii) to parameter (i) can be plotted on the abscissa. This results in various measuring ranges (fields in the diagram) for the various iron states and iron overloading can be distinguished from a normal iron status, and a normal iron status can be distinguished from iron deficiency and also from iron distribution disturbances such as tumour anaemia, chronic anaemia, rheumatoid arthritis or renal anaemia.

The method according to the invention can also be used to specify in a simple manner the treatment required for the respective patient depending on the determined iron status. Thus for example erythropoietin (EPO) therapy is indicated for a classification in group (A), blood letting is indicated for a classification in group (B), no therapy is indicated for a classification in group (C) and iron substitution is indicated when classified in group (D). These therapeutic recommendations are based on the fact that erythropoiesis is mainly regulated by the growth factor EPO and by iron, and the various types of iron metabolism disorders require different treatments that can be determined by the method according to the invention. An iron deficiency leads in particular to a deficit in haemoglobin formation, to hypochromic mycrocytes/anulocytes and thus to anaemias which are manifested as iron deficiency and chronic bleeding. Deficiency of erythropoietin (EPO) results in a reduced proliferation and thus to anaemias that manifest themselves as iron distribution disturbances, acute phase conditions, infections, chronic inflammation, tumour anaemias and renal anaemias.

In addition to the treatment of disorders of iron metabolism, the method according to the invention also allows observation or/and monitoring of the progress and response to treatment and thus ensures an optimal use of EPO or iron preparations (e.g. oral or parenteral iron preparations) in individual patients.

Depending on the selected characteristic values of the above mentioned parameters, the method according to the invention also allows a sex-specific discrimination or differentiation of the individual iron status in which the normal values or cut-off values can then be established for each sex (male or female).

Surprisingly, it was found that chronic diseases, even in very early stages, result in a classification in group (A). Thus, chronic diseases and chronic inflammatory diseases can be diagnosed with the method according to the invention. In particular, diseases such as renal insufficiency, malignancies, rheumatoid arthritis, diabetes, heart failure, cardiovascular diseases, thrombosis, neurogenerative diseases or impaired pregnancies can be identified, and respective treatments can be indicated by the present invention.

Group (B) indicating iron overloading includes haemochromatosis such as sickle cell anemia or HFE gene modifications.

The invention is elucidated in the following on the basis of particularly preferred embodiments; however, it should be noted that the inventive procedure is not limited to the parameters mentioned as examples.

In a first preferred embodiment sTfR is determined as parameter (ii). Surprisingly it was found that the soluble transferrin receptor (sTfR) is a parameter for the following three types of iron status:
(a) haemoglobin synthesis rate,
(b) repletion status of the iron stores (ferritin) and
(c) non-ferritin iron deposition (disturbance in distribution, iron deposition).

In addition it is preferred that the ferritin content is determined as parameter (i). A combination of sTfR and ferritin yields information on the depletion of iron stores, haemoglobin synthesis and iron deposition as shown in FIG. 1.

These two parameters for determining the iron status i.e. sTfR and ferritin can now be combined in a preferred embodiment of the method according to the invention with a further biochemical marker or a haematological marker.

The inflammation marker CRP or the marker SAA and most preferably the marker CRP is used as the biochemical marker.

This combination can serve in particular as diagnostic markers for chronic anaemias (ACD) in rheumatic diseases.

In order to efficiently differentiate between the anaemias, the classification is carried out by calculating the ratio of sTfR/log ferritin. It is standardized on the basis of the CRP value. For the graphic representation the ratio of sTfR/log ferritin is plotted on the X axis and the CRP value is plotted on the Y axis.

The cut-off values shown are derived from the reference ranges for women (premenopausal) for sTfR of 1.9 to 4.4 mg/l, ferritin of 15 to 150 µg/l and CRP of <5 mg/l and for mean for sTfR of 2.2 to 5.0 mg/l, ferritin of 30 to 400 µg/l and CRP of <5 mg/l. When this is represented graphically results in four quadrants which are defined by the cut-off values for CRP of 5 mg/l and for the ratios sTfR/log ferritin of 3.4 (men) and 3.7 (women) and 0.9. This enables anaemias which are caused by perturbations of iron distribution (A), iron deficiency (D) and iron overloading (B) to be distinguished from the normal iron status (c).

In a particularly advantageous embodiment of the invention the differential diagnosis of the important disorders of iron metabolism is assisted by a software program which enables a mathematical linkage of the three above-mentioned independent parameters. The following independent parameters are preferably used:
  (i) ferritin as a parameter that allows an estimate of the actual body iron stores (depot iron),
  (ii) sTfR as a parameter which allows an estimation of the erythropoietic activity (functional iron) and
  (iii) CRP as a parameter for the diagnosis of unspecific disorders of iron metabolism which are caused for example by inflammatory processes.

In this manner the method according to the invention enables disorders of iron metabolism to be described by using the iron storage protein ferritin and the soluble transferrin receptor as an indicator for the iron requirements of the cells. In addition the determination of the soluble transferrin receptor enables an estimate of the erythropoietic activity. CRP acts as an indicator of a persistent acute phase reaction. The correlation between CRP and the ratio of sTfR/log ferritin allows an efficient differential diagnosis of anaemias such as iron deficiency, iron distribution disorders and iron overloading from normal iron status. The differential diagnosis can be further simplified for the user by a computer-aided evaluation program.

A latex-enhanced immunoturbidimetric assay can for example be used to determine the soluble transferrin receptor for use in a method in combination with the determination of ferritin and CRP. The values for sTfR stated herein in connection with methods using sTfR, ferritin and CRD refer to values measured with latex-enhanced immunoturbidimetric assays. The latex-enhanced immunoturbidimetric assay have an adequately sensitive measuring accuracy for detecting the relatively low concentrations of soluble transferrin receptor in the blood plasma (<10 mg/l, or <100 nmol/l). Since international reference methods and reference preparations are not yet available for sTfR, reference intervals on the COBAS INTEGRA® and Roche/Hitachi were determined for the test described herein and the sTfR reference range was 2.2 to 5.0 (2.5 to 97.5 percentile) for men and 1.9 to 4.4 for women.

According to the invention the cut-off value for sTfR/log ferritin which discriminates between the iron status of iron overloading and normal iron status is 0.7 to 1.4, in particular 0.8 to 1.0 and most preferably 0.9. The cut-off value with which iron deficiency can be distinguished from iron distribution disorders and normal iron status is preferably 3.0 to 4.0, more preferably 3.4 to 3.7 and most preferably at about 3.4 for men and at about 3.7 for women. Calibration to determine these values was made as described by S.Kolbe-Busch et al., Clin.Chem.Lab.Med.40(5) (2002), 529-536. sTFR from placenta was used as standard thereby. The cut-off value for CRP above which an acute phase reaction is defined, is preferably at about 1 to 10 mg/l, more preferably at 4 to 6 mg/l and in particular at about 5 mg/l.

In a further most preferred embodiment a haematological parameter is determined as parameter (iii) and in particular the proportion of hypochromic red blood cells (HRC %) or the haemoglobin content of reticulocytes (CHr). It was surprisingly found that these parameters are new indicators for functional iron deficiency. These parameters can be used in addition to biochemical markers such as ferritin, transferrin saturation (TfS) and transferrin receptor (TfR) to identify an iron deficiency (ID).

The haematological parameters show rapidly and directly any change in erythropoietic activities.

Non-anaemic patients without APR (acute phase reaction) have a CHr of $\geq 28$ pg and HCR of $\leq 5\%$. Patients with a CHr of <28 pg or a HCR of >5% were classified as functionally iron deficient. Serum ferritin, TfS, TfR and the calculated parameters TfR-F index (ratio TfR/log ferritin) and Tf-Tf-R product enable a reliable diagnosis of iron deficiency in comparison with HCR % and CHr in patients without APR. In the case of anaemias without APR which are often observed in infections, inflammation or tumours, the diagnostic effectiveness of the said biochemical markers ferritin and transferrin receptor is often inadequate. A combination of these biochemical markers with haematological markers such as CHr considerably improves the results. When CHr is plotted against the TfR-F index or against the Tf-TfR product, it is possible to classify anaemias in patients with and without APR inter alia into the following categories: no functional iron deficiency, functional iron deficiency combined with depleted iron stores and functional iron deficiency combined with replete iron stores.

This embodiment of the invention enables an identification of iron deficiency and a distinction of iron deficiency from other disorders of iron metabolism, in particular so-called anaemias, from chronic diseases (ACD) which accompany infections, inflammation or tumours. ACD is characterized by an inadequate erythropoietin production, inhibition of the proliferation of erythrocyte precursor cells in the bone marrow and disturbances of iron utilization. As in iron deficiency anaemia (IDA), functional iron deficiency in ACD is one of the main distinguishing factors from erythropoiesis. It is defined as an imbalance between iron requirements in the erythroid bone marrow and iron supply which is not sufficient to ensure a normal haemoglobination of red blood cells. This results in a reduced haemoglobin concentration in reticulocytes and erythrocytes. In IDA the iron supply depends on the content of the iron stores, and in the case of ACD on the rate of its mobilization. In ACD a functional iron deficiency can occur even in the presence of large iron stores if the iron release is impaired.

The diagnosis of a functional iron deficiency is important for the correct treatment of the patients. However, in practice it is often only possible to classify the patients as iron deficient, non-iron deficient or potentially iron-deficient. The third group of patients which are typically those with an acute phase reaction (APR) or a cancer related anaemia (CRA) have previously required an examination of their bone marrow in order to determine the type of disease.

Usually biochemical markers of iron metabolism are used such as serum or plasma iron, transferrin, % transferrin saturation (TfS), ferritin and serum-circulating transferrin receptor (TfR). The diagnosis of IDA is based on the presence of anaemia and morphological features of erythrocytes (hyperchromia, mycrocytosis) in conjunction with a low serum ferritin and a reduced transferrin saturation. The diagnosis of ID in conjunction with normal serum ferritin contents may, however, be difficult in the case of ACD. Ferritin is an acute phase reactant, transferrin is a negative acute phase reactant and the concentration of both proteins is influenced by various conditions. An increase in TfR which is a useful indicator for iron deficiency, can also occur in patients with an increase in the number of red precursor cells in the bone marrow. Due to these difficulties it is necessary to provide clinical laboratory tests which measure the functional availability of iron for haemoglobin synthesis especially in the red blood cells and their precursors.

A marker which can be used to assess the functional iron status, is the measurement of the proportion of hypochromic red cells (HRC %). Due to the life time of erythrocytes of about 120 days, HCR % integrates information over a long period and is thus a late indicator for iron-limited erythropoiesis. A value for HCR of <10% in conjunction with low serum ferritin indicates that the iron supply for erythropoiesis is sufficient to enable a normal haemoglobination of red cells.

The cellular haemoglobin content of reticulocytes (CHr) is an early marker for functional iron deficiencies since reticulocytes exist in the circulation for only 1 to 2 days. The utility of this index for monitoring the erythropoietic function in order to assess the iron status, to diagnose an iron deficiency and to diagnose and treat various haematological diseases is known.

A combination of the haematological indices HRC % or/and CHr with biochemical markers is described here for the first time.

Using the 2.5 and 97.5 percentiles of the control group, the following cut-offs were determined for the present invention: 3 to 7%, in particular 4 to 6% and most preferably about 5% for HCR and 25 to 30 pg, in particular 27 to 29 pg and particularly preferably about 28 pg for CHr. The iron status can preferably be classified using a diagnostic plot in which CHr is plotted against TfR-F or against Tf-Tf-R. In this manner the iron status can be divided into various categories and in particular four categories i.e. normal iron status, iron deficiency (CRP normal), iron deficiency (CRP increased) and iron distribution disorder.

In a further preferred embodiment the invention relates to a method for determining the iron status and, in particular, for detecting disorders of iron metabolism comprising the determination of (i) a parameter which allows determination of the total body iron stores, (ii) a parameter which allows determination of the erythropoietic maturation process and/or its activity, (iii) a parameter which allows determination of unspecific disorders of iron metabolism, in particular, a biochemical parameter, and (iv) a haematological parameter, in particular, MCH or CHr.

In this embodiment group (A) concerning patients who probably have disturbances of iron distribution (acute deficiency of functional iron) can be further divided in two groups. In particular, patients having no acute deficit of functional iron can be distinguished from patients actually having functional iron deficiency or disturbance of iron distribution. MCH or CHr can be determined from blood count. MCH is the average hemoglobin content of an erythrocyte cell and is reduced, if an acute deficiency of functional iron and thus a disturbance of iron distribution occurs. Therefore, MCH can be used to distinguish a deficiency of functional iron from other conditions. 28 pg/cell is to be regarded as a limiting value of MCH and CHr, whereby no acute deficiency of functional iron is the case for values above that value and deficiency of functional iron is diagnosed, if values are lower.

The invention further relates to a test strip for performing the inventive method. Such a test strip comprises means for the determination of (i) a parameter which allows determination of the total body iron stores, (ii) a parameter which allows determination of the erythropoietic maturation process and/or its activity, and (iii) a parameter which allows determination of unspecific disorders of iron metabolism.

In a preferred embodiment, for example, CRP will be determined competitively and the other two parameters by using a sandwich assay.

The invention is further elucidated by the attached figures and examples

EXAMPLES

Example 1

163 patients were examined using the parameters CRP and sTfR/log ferritin and classified according to the results obtained as normal iron status, iron deficiency, iron distribution disturbance or iron overloading. The combined determination of the three parameters sTfR, ferritin and CRP proved to be highly suitable for differential diagnosis.

Example 2

373 patients were examined using a combination of haematological parameters and biochemical parameters and classified into four groups. Group N is the control group and contained non-anaemic patients without APR. Group A consists of anaemic patients without APR. Group AA contains anaemic patients with APR in combination with CRA, ACD or an acute infectious or inflammatory disease. The patient group NA contains non-anaemic patients with APR.

Ferritin was determined on a Cobascore analyzer from Roche Diagnostics, Mannheim, Germany and the reference range was determined as 20 to 150 µg/l for women and 20 to 350 µg/l for men. TfR was determined in each sample using commercial assays. The analytical principle of the assay is based on microagglutination of latex particles which are coated with a monoclonal anti-TfR antibody (Dade Behring, Marburg, Germany). In this manner a latex-enhanced nephelometric test is carried out. The reference range (2.5 to 97.5 percentile) was 0.4 to 1.8 mg/l.

TfS was calculated using the formula TfS (%)=Fe (µg/l)× 7.09/Tf (g/l).

In order to determine disorders of iron metabolism CHr and HRC % were determined as indicators of an iron deficient erythropoiesis as a plot against the TfR-F index. The following results were obtained for the individual patient groups.

N group (non-anaemic group without APR)

The control group consisted of 71 patients which were found in quadrant 1 (left top, FIG. 3) in the diagnostic blots comprising 4 quadrants.

A group (anaemic group without APR)

Figure 3:
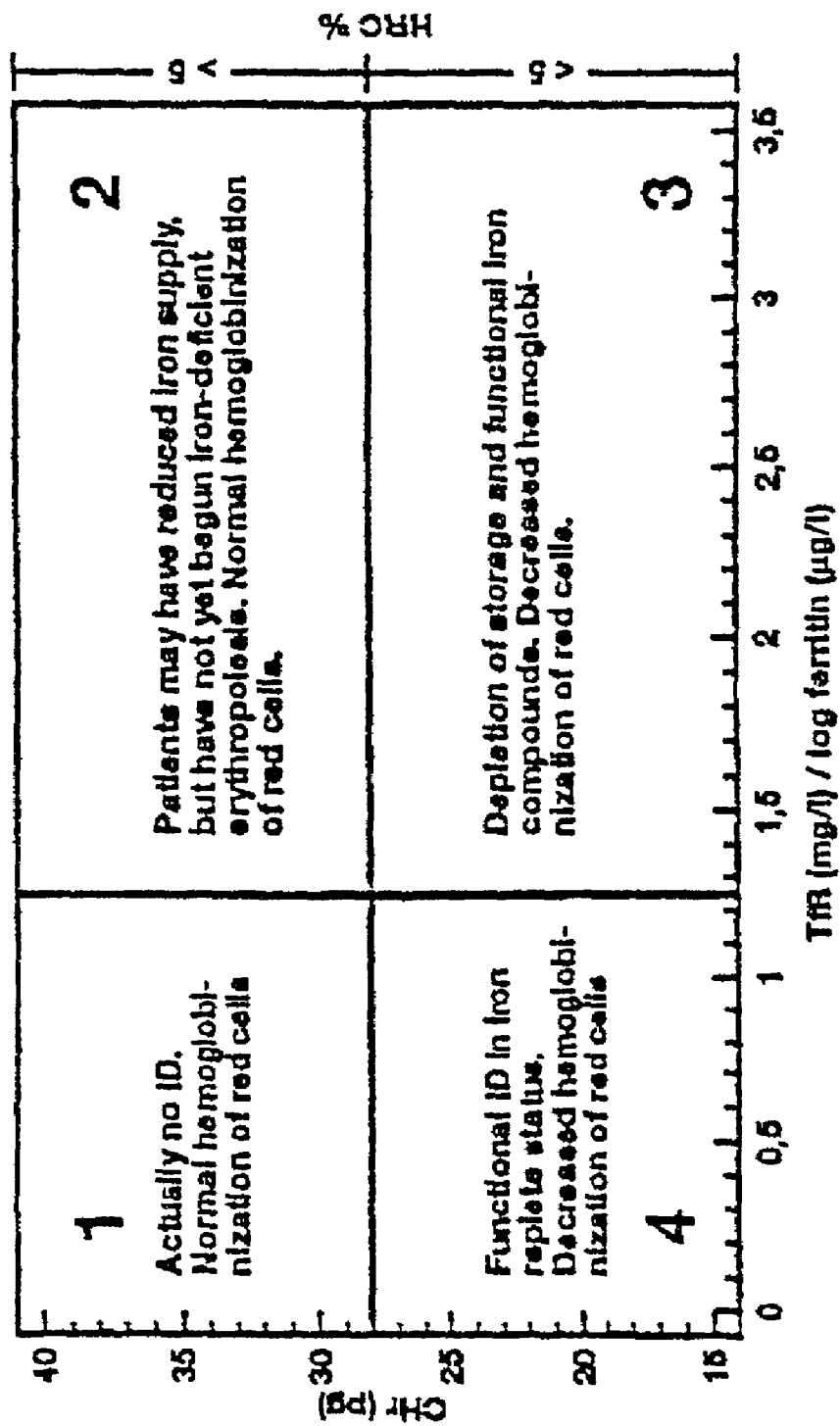
FIG. 3 shows the classification used in a combination of haematological and biochemical markers.
Figure 4:
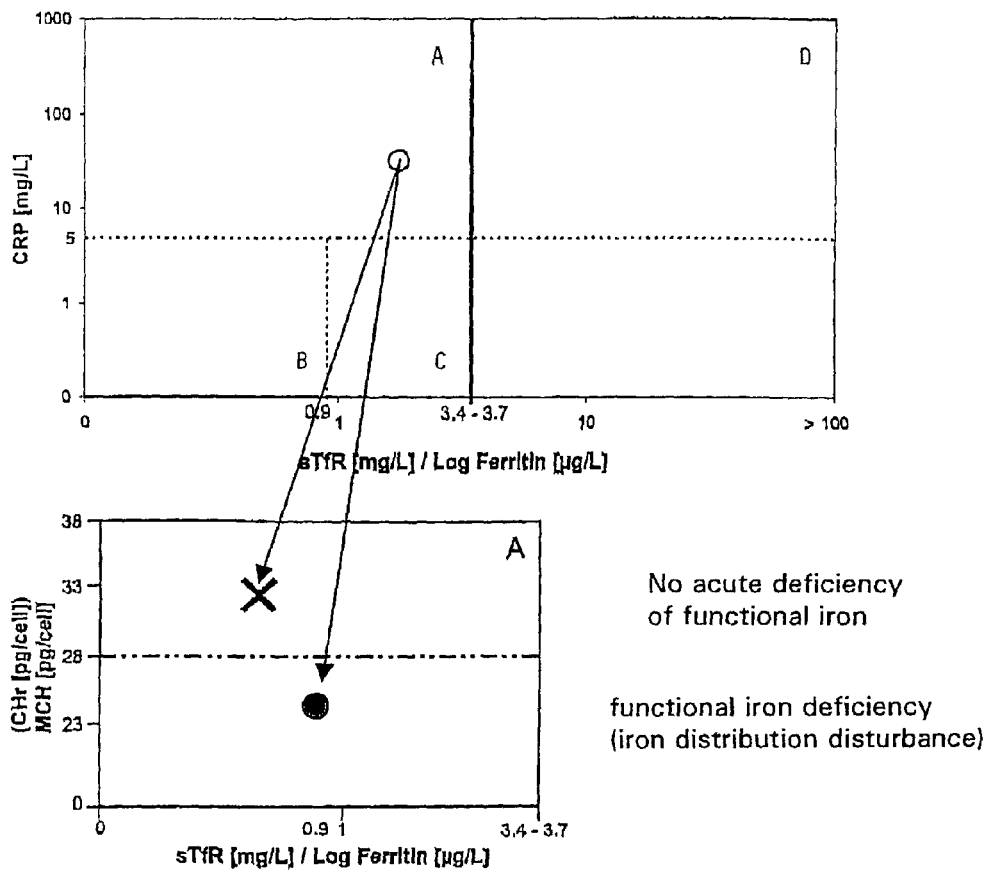
FIG. 4 shows a preferred embodiment according to the invention, wherein group (A) is further divided by determination of a haematological parameter, in particular, of MCH or CHr.

79 anaemic patients without APR were examined and assigned to quadrant 2 (FIG. 3).

NA group (non-anaemic group with APR)

This group consisted of 80 patients which were classified in quadrant 4 (FIG. 3).

AA group (anaemic group with APR)

This group consisted of 143 patients which were classified in quadrant 3 (FIG. 3).

Patients with data points in quadrant 1 had a CHr of ≧28 pg.

Patients in quadrant 2 are iron-deficient according to the TfR-F index. All patients in this quadrant have a CAA and HRC>5%. The pattern CHr>288 pg, HRC>5%, elevated TfR and normal or elevated ferritin indicated that these patients with CRA and APR have a reduced iron supply as indicated by the increase in TfR which, however, was not sufficient to cause a functional iron deficiency.

Patients with data points in quadrant 3 had the lowest ferritin and highest Tf concentrations. Tf is a negative acute phase reactant and the mean concentration was reduced in patients with an iron replete status in quadrants 1 and 4. In patients of quadrant 3 with haematological and biochemical identified iron deficiency, APR did not, however, cause a decrease in the serum Tf which indicates that the positive stimulus of iron deficiency is larger than the negative stimulus of APR on Tf synthesis.

The patients with data points in quadrant 4 had a CHr of <28 pg and a HRC of >5%.

In summary this means that the allocation of the data points to one of the quadrants 1 to 4 in the diagnostic plot denotes the following for the identification of iron deficiency in the diagram CHR against TfR/log ferritin:

Quadrant 1: no biochemical or haematologically identified iron deficiency
Quadrant 2: only biochemically identified iron deficiency
Quadrant 3: biochemically and haematologically identified iron deficiency
Quadrant 4: only haematologically identified iron deficiency.

The patient groups can be subdivided as follows according to the haematological and biochemical results:

Group N: non-anaemic, no APR; Hb (men)$\geq$140 g/l, Hb (women)$\geq$123 g/l, CRP$\leq$5 mg/l, WBC$\leq$10,000/µl, ESR (erythrocyte sedimentation rate)$\leq$30 mm/h, RDW (red cell distribution width)$\leq$15%;

Group A: anaemic, no APR; Hb (men)<140 g/l, Hb (women)<123 g/l, CRP$\leq$5 mg/l, WBC$\leq$10,000/µl; ESR$\leq$30 mm/h;

Group NA: non-anaemic with APR; Hb (men)$\geq$140 g/l, Hb (women)$\geq$123 g/l, CRP>5 mg/l or WBC>10,000/µl or ESR>30 mm/h or RDW>15%;

AA: anaemic with APR: Hb (men)<140 g/l, Hb (women) <123 g/l, CRP>5 mg/l or WBC>10,000/µl or ESR>30 mm/h.

What is claimed is:

1. A method for classifying iron status of a patient and treating the patient in need of treatment, the method comprising:
    (a) determining a level of each of the following in one or more samples from a patient:
        (i) ferritin,
        (ii) sTfR,
        (iii) CRP, and
        (iv) optionally CHr or MCH;
    (b) plotting sTfR/log ferritin on a first axis of a plot and CRP on a second axis of the plot, the plot divided into quadrants, the quadrants defining specific iron status classifications of:
        (A) iron distribution disorders or/and iron utilization disorders with acute phase reaction,
        (B) iron overloading,
        (C) normal iron status, and
        (D) deficiency of storage iron;
    (c) determining the iron status classification of the patient; and
    (d) treating a patient having the iron status classifications A, B, or D.

2. The method of claim 1, wherein the treatment specific for the iron status classification comprises EPO therapy for patients classified in group (A), blood letting for patients classified in group (B), and iron substitution for patients classified in group (D).

3. The method of claim 1, further comprising monitoring progress and response to the treatment wherein the monitoring comprises repeating steps (a) to (d).

4. The method of claim 1, further differentiating the iron status classification of iron distribution disorders or/and iron utilization disorders with acute phase reaction by evaluating the level of CHr or MCH.

5. The method of claim 4, wherein the iron status classification of iron distribution disorders and/or iron utilization disorders with acute phase reaction is further classified as either functionally iron deficient when the level of CHr or MCH or both is less than 28 pg/cell or not acutely functionally inn deficient when the level of CHr or MCH is above 28 pg/cell.

6. The method of claim 1, wherein the iron status of the patient is classified as an iron distribution disorders and/or iron utilization disorders with acute phase reaction when sTfR/log ferritin is less than 3.4 (male) or 3.7 (female), and CRR (mg/L) is greater than 5.

7. The method of claim 1, wherein the iron status of the patient is classified as iron overloading when sTfR/log ferritin is less than 0.9 and CRP (mg/L) is less than 5.

8. The method of claim 1, wherein the iron status of the patient is classified as normal iron status when sTfR/log ferritin ranges from 0.9 to 3.7 (female) and 0.9 to 3.4 (male) and CRP (mg/L) is less than 5.

9. The method of claim 1, wherein the iron status of the patient is classified as a deficiency in storage iron when sTfR/log ferritin is greater than 3.4 (male) or 3.7 (female).

10. A method for identifying iron deficiency in a patient and treating the patient in need of treatment, the method comprising:
    (a) determining a level of each of the following in one or more samples from a patient:
        (iv) ferritin,
        (v) sTfR, and
        (vi) CHr;
    (b) plotting sTfR/log ferritin on a first axis of a plot and CHr on a second axis of the plot, the plot divided into quadrants, the quadrants defining specific iron deficiency classifications of:
        (1) no biochemical or haemotologically identified iron deficiency,
        (2) biochemically identified iron deficiency,
        (3) biochemical and haemotologically identified iron deficiency, and
        (4) haemotologically identified iron deficiency;
    (c) determining the iron deficiency classification of the patient; and
    (d) treating a patient for iron deficiency depending on the iron deficiency classification of the patient.

11. The method of claim 10, wherein the patient is classified as having (1) no biochemical or haemotologically identified iron deficiency or (2) biochemically identified iron deficiency when the level of CHr is equal to or greater than 28 pg/cell.

12. The method of claim 10, wherein the patient is classified as having (3) biochemical and haemotologically identified iron deficiency or (4) haemotologically identified iron deficiency when the level of CHr is less than 28 pg/cell.

* * * * *

UNITED STATES PATENT AND TRADEMARK OFFICE
CERTIFICATE OF CORRECTION

| | | |
|---|---|---|
| PATENT NO. | : 7,601,684 B2 | Page 1 of 1 |
| APPLICATION NO. | : 10/242061 | |
| DATED | : October 13, 2009 | |
| INVENTOR(S) | : Roddiger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this

Fifth Day of October, 2010

David J. Kappos
*Director of the United States Patent and Trademark Office*